United States Patent
Akahoshi

[19]

[11] Patent Number: 6,106,786
[45] Date of Patent: Aug. 22, 2000

[54] AROMA APPARATUS

[75] Inventor: Ryoichi Akahoshi, Kawagoe, Japan

[73] Assignee: Futaba Denshi Kogyo K.K., Mobara, Japan

[21] Appl. No.: 09/222,819

[22] Filed: Dec. 30, 1998

[30] Foreign Application Priority Data

Jan. 14, 1998 [JP] Japan .................................. 10-005858

[51] Int. Cl.[7] .................................. A61L 9/03; A61L 9/04
[52] U.S. Cl. .......................... 422/124; 422/123; 422/125; 422/305; 422/306; 392/386; 222/187; 261/DIG. 17; 261/DIG. 65
[58] Field of Search .................................. 422/4, 5, 120, 422/123–125, 305, 306; 392/386; 222/187; 261/DIG. 65, DIG. 17

[56] References Cited

U.S. PATENT DOCUMENTS

| | | | |
|---|---|---|---|
| 577,442 | 2/1897 | Miranda | 422/125 |
| 1,944,821 | 1/1934 | Blaise | 422/125 |
| 2,899,722 | 8/1959 | Adams | 422/125 |
| 4,346,059 | 8/1982 | Spector | 422/125 |
| 5,534,229 | 7/1996 | Nomura et al. | 422/123 |

*Primary Examiner*—Robert J. Warden, Sr.
*Assistant Examiner*—Fariborz Moazzam
*Attorney, Agent, or Firm*—Oblon, Spivak, McClelland, Maier & Neustadt, P.C.

[57] ABSTRACT

A blowing type aroma apparatus, involving no danger of fire and being capable of providing a natural aroma. A body of the aroma apparatus has an opening in its upper surface. A container for containing a liquid aromatic and a cylinder surrounding this container and having open upper and lower ends are located in the opening. An impregnator impregnated with the aromatic is disposed in the container. An axial flow fan is housed beneath the opening within the body and the air flow generated by the axial flow fan passes through the support member and flows into a space between the cylinder and the container. The air becomes a laminar flow and rises in the space between the cylinder and the container. The air flow permits the volatilization of the aromatic contained in the impregnator, whereby the aroma is diffused from the opening at the upper end of the cylinder.

10 Claims, 1 Drawing Sheet

AROMA APPARATUS

BACKGROUND OF THE INVENTION

The present invention relates to an aroma apparatus for volatilizing a liquid aromatic or an essential oil in order to enjoy an aroma privately in the home or for use in aromatherapy or the like.

Many types of conventional general aroma apparatus include a small plate which is intended to receive an aromatic or an essential oil and which is located over a heat source such as a candle or a small electric bulb. The aromatic or the essential oil is then volatilized by the use of light and heat from the heat source.

In this conventional type of aroma apparatus, the aromatic or the like is heated so that warm aromatic vapor is raised. However, the fragrance is deteriorated by the heating, it is different from a comfortable natural aroma. Also, there is the danger of fire which has been caused by this type of aroma apparatus.

An object of the present invention is to provide an aroma apparatus involving no danger of fire, and which is capable of providing a natural aroma. It is a further object of the invention to facilitate the replacement and replenishment of the aromatic, while maintaining an attractive appearance.

SUMMARY OF THE INVENTION

According to the present invention, there is provided an aroma apparatus which comprises a container for containing a liquid aromatic; an impregnator disposed in the container and impregnated with the aromatic; and blowing means for generating an air flow over the impregnator, thereby volatilizing the aromatic.

According to a second aspect of the present invention, there is provided an aroma apparatus which comprises a container for containing a liquid aromatic; an impregnator disposed in the container and impregnated with the aromatic; a cylinder for housing the container; and blowing means for generating an upward laminar flow between the container and the cylinder.

According to a third aspect of the present invention, there is provided an aroma apparatus which comprises a body having an opening in the upper surface thereof; a container located in the opening of the body, for containing a liquid aromatic; an impregnator disposed in the container and impregnated with the aromatic; a cylinder whose upper and lower portions are opened, the cylinder being located in the opening of the body so as to house the container; and blowing means located under the opening within the body, for generating an upward laminar flow between the container and the cylinder.

Preferably, the impregnator has a cylindrical shape and is open at both its upper and lower end. The impregnator also preferably has; a cylindrical shape whose upper and lower ends are closed and opened, respectively, and the impregnator has an opening in its peripheral surface. The rate of air flow generated by the blowing means is advantageously, and container is made of a glass. The cylinder may also be made of a glass. Preferably, illuminating means are disposed within the body so that a light may escape from the opening.

DETAILED DESCRIPTION OF THE PREFERRED EMBODIMENTS

Figure 1:
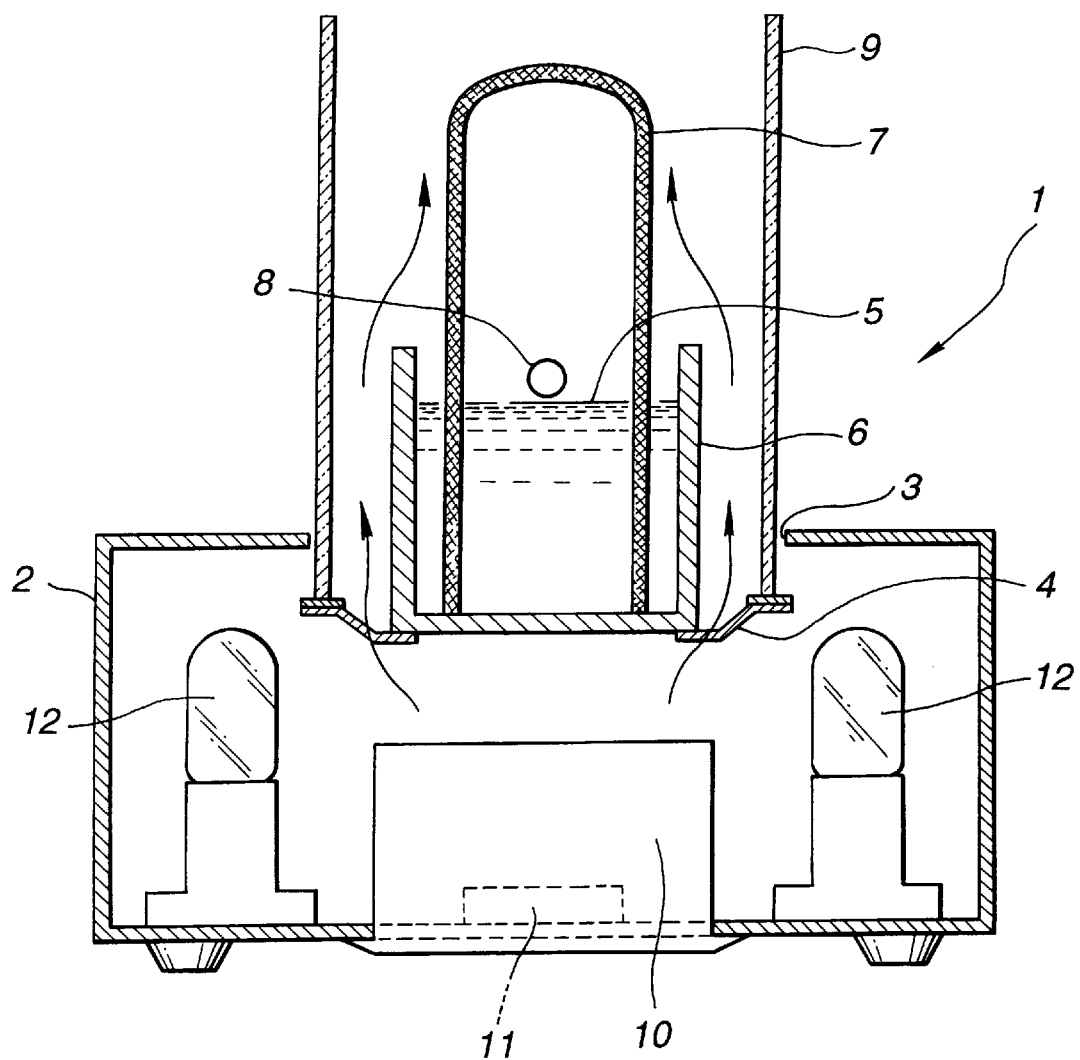
FIG. 1 is a sectional view showing a structure of an aroma apparatus of a first example of an embodiment of the present invention.

An example of an embodiment of the present invention will be described with reference to FIG. 1.

The aroma apparatus 1 includes a body 2 comprising a stainless plate, iron plate, aluminum plate or the like. The surface of the body 2 is finished in any desired color. A substantially circular opening 3 is formed in the center of the upper surface of the body 2. A supporting member 4, whose center is opened, is disposed within the body 2 near the opening 3.

A container 6 for containing a liquid aromatic 5 is placed in the opening 3 of the body 2. The lower part of the container 6 is inserted in the body 2, and the bottom surface of the container 6 is supported by the supporting member 4. The container 6 is made of a glass or a metal of any chosen color. The container 6 has a cylindrical shape with an open upper surface. Plastic materials tend not to be suitable as a material for the container 6 because it could generally be deteriorated by the aromatic. This container 6 can, of course, be of any favorite design. The aromatic 5 to be contained in the container 6 will also be selected in accordance with personal taste.

An impregnator 7 is located in the container 6. The impregnator 7 of this embodiment is substantially cylindrical. The upper and lower ends of the impregnator 7 are closed and open, respectively. An air vent hole 8 is formed in the peripheral surface of the impregnator 7. Even when the impregnator 7 is immersed in the container 6 containing the aromatic 5 with its open end downwards, the liquid levels are the same inside and outside the impregnator 7 because the air can escape from the hole 8. The impregnator 7 can be made from any suitable material such as filter paper, ceramic, cellulose or glass fiber. Any material could be selected for the impregnator 7, provided it can absorb and retain the liquid aromatic, is not subject to significant erosion by the aromatic and it does not have its own very strong smell. If the upper end of the impregnator 7 is also open, the hole 8 in the peripheral surface may be omitted. The larger the surface area of the portion above the liquid level of the aromatic 5, the more easily the aromatic 5 will be volatilized. For this reason, the dimension and surface area of this portion are appropriately set in accordance with conditions.

A cylindrical cylinder 9, whose upper and lower ends are opened, is located in the opening 3 of the body 2 so that it may house the container 6. The lower part of the cylinder 9 is inserted in the body 2, and the bottom surface of the cylinder 9 is supported by the supporting member 4. The cylinder 9 is made of the glass of any desired color. The upper end of the cylinder 9 is above the upper end of the impregnator 7 in the container 6. The container 6 and the impregnator 7 are completely surrounded by the cylinder 9. In accordance with personal taste, other shapes may be used such as a polygonal cylinder, any decoration may be applied to the surface of the cylinder 9, and any color may be selected.

An axial flow fan 10 is located as a blowing means beneath the opening 3 within the body 2. The axial flow fan 10 is driven by a power source (e.g. of 100 V) so that it generates an air flow upwards. The rate of air flow can be optionally adjusted by air flow rate adjusting means 11 such as a volume disposed in the body 2. The air flow rate adjusting means 11 is operated by a dial or the like (not shown) disposed on the outer surface of the body 2. The axial flow fan 10 generates an upward laminar flow between the container 6 and the cylinder 9. Any fan other than the axial flow fan may be used as the blowing means provided that it generates a laminar flow.

One or more illuminating means 12 is/are disposed within the body 2. The illuminating means 12 are activated by the power source (e.g. of 100 V). The light level from the illuminating means 12 can be optionally adjusted by light level adjusting means such as the volume (not shown) disposed in the body 2. The light level adjusting means is operated by a dial or the like (not shown) disposed on the outer surface of the body 2. This illuminating means 12 is located in proximity to the clearance between the opening 3 and the supporting member 4 so that the light may escape from the opening 3.

The axial flow fan 10 is driven in the aroma apparatus 1 arranged as described above. The air flow generated by the axial flow fan 10 passes through the support member 4 and flows into the space between the cylinder 9 and the container 6. The air flow changes into a laminar flow pattern and rises in the space between the cylinder 9 and the container 6. Such an air flow causes the volatilization of the aromatic 5 contained in the impregnator 7. Consequently, an aroma is diffused into the immediate environment from the opening in the upper end of the cylinder 9.

In an approach in which the aromatic liquid is directly vaporized by heat, the generated aroma tends to be too strong. However, with a method of volatilizing the aromatic 5 contained in the impregnator 7 by a laminar air flow as in this embodiment of the present invention, the generated aroma is natural.

When the illuminating means 12 is activated, light from the illuminating means 12 passes through the lower end of the cylinder 9 and the bottom surface of the container 6 and then escapes from the body 2. Thus, when the cylinder 9 and container 6 are made of glass, they are beautifully illuminated by the light. As a result, the aroma apparatus 1 constitute an excellent interior decoration. In the case of a low indoor temperature or the like, the indirect heat from the illuminating means 12 acts on the aromatic 5 in an auxiliary fashion, thereby helping vaporization.

According to the aroma apparatus 1 of this embodiment, the cylinder 9 and the container 6 are positioned on the upper surface of the body 2 and thus can be removed. It is therefore possible to replace the cylinder 9 and the container 6 easily by the ones of different design, color or the like, depending on one's inclination. Moreover, it is easy to replenish the container 6 with the aromatic 5.

Thus, the impregnator is disposed in the container for the aromatic, this impregnator is surrounded by the cylinder whose upper and lower portions are open, and the blowing means is used to generate the upward laminar flow between the container and the cylinder, whereby the aromatic is naturally volatilized. According to the present invention, it is therefore possible to obtain various advantages which have not been obtained by the aroma apparatus of the prior art: no danger of fire, the ability to provide the enjoyment of the natural aroma the easy replacement and replenishment of the aromatic and an excellent appearance.

What is claimed is:

1. An aroma apparatus comprising:

a container for containing a liquid aromatic;

an impregnator disposed in the container and impregnated with the aromatic, said impregnator being cylindrical in shape; and a blower for generating an air flow over the circumferential surface of the impregnator, thereby volatilizing the aromatic from the surface of the impregnator.

2. An aroma apparatus as claimed in claim 1, further including a cylinder housing the container, said cylinder and said container being supported by a supporting member, and the blower being arranged to produce an air flow passing through the supporting member to generate an upward laminar flow between the container and the cylinder.

3. An aroma apparatus as claimed in claim 2, further comprising:

a body having an opening in an upper surface thereof, the container being located in the opening of the body, wherein the cylinder, whose upper and lower portions are open, is located in the opening of the body thereby housing the container, the blower being located beneath the opening within the body, thereby generating the upward laminar flow between the container and the cylinder.

4. An aroma apparatus as claimed in claim 1, in which the impregnator has a cylindrical shape and is open at upper and lower ends thereof.

5. An aroma apparatus as claimed in claim 1, in which the impregnator has a cylindrical shape, has upper and lower ends which are closed and open, respectively, and the impregnator has an opening in a peripheral surface thereof.

6. An aroma apparatus as claimed in claim 1, wherein the blower comprises an adjustable blower for adjusting the rate of air flow generated by said adjustable blower.

7. An aroma apparatus as claimed in claim 1, wherein the container is made of a glass.

8. An aroma apparatus as claimed in claim 2, wherein the cylinder is made of a glass.

9. An aroma apparatus as claimed in claim 3, including an illuminating degree disposed within the body so that light may escape from the opening.

10. An aroma apparatus as claimed in claim 1, wherein said blower generates an air flow parallel to a direction of conveying of said aromatic by capillary action in the impregnator.

* * * * *

UNITED STATES PATENT AND TRADEMARK OFFICE
CERTIFICATE OF CORRECTION

PATENT NO. : 6,106,786
DATED : August 22, 2000
INVENTOR(S) : Ryoichi AKAHOSHI, et al.

It is certified that error appears in the above-identified patent and that said Letters Patent is hereby corrected as shown below:

On the title page, item [73] should read: -- Futaba Denshi Kogyo K.K., Mobara, Japan part interest --

Signed and Sealed this

Twenty-second Day of May, 2001

*Attest:*

NICHOLAS P. GODICI

*Attesting Officer*   Acting Director of the United States Patent and Trademark Office